US012260552B2

(12) United States Patent
Aoyama et al.

(10) Patent No.: US 12,260,552 B2
(45) Date of Patent: Mar. 25, 2025

(54) DETERMINATION DEVICE

(71) Applicant: LIXIL Corporation, Tokyo (JP)

(72) Inventors: Hiroshige Aoyama, Tokyo (JP); Kenta Tanaka, Tokyo (JP); Hiroto Miwa, Ashiya (JP)

(73) Assignee: LIXIL Corporation, Tokyo (JP)

( * ) Notice: Subject to any disclaimer, the term of this patent is extended or adjusted under 35 U.S.C. 154(b) by 403 days.

(21) Appl. No.: 17/763,179

(22) PCT Filed: Sep. 18, 2020

(86) PCT No.: PCT/JP2020/035405
§ 371 (c)(1),
(2) Date: Mar. 23, 2022

(87) PCT Pub. No.: WO2021/060174
PCT Pub. Date: Apr. 1, 2021

(65) Prior Publication Data
US 2022/0375080 A1 Nov. 24, 2022

(30) Foreign Application Priority Data
Sep. 24, 2019 (JP) ................................. 2019-173484

(51) Int. Cl.
*G06T 7/00* (2017.01)
*G06V 10/62* (2022.01)
(Continued)

(52) U.S. Cl.
CPC ............ *G06T 7/0012* (2013.01); *G06V 10/62* (2022.01); *G06V 10/764* (2022.01); *E03D 9/00* (2013.01);
(Continued)

(58) Field of Classification Search
CPC ......... G06T 7/0012; G06T 2207/20081; G06T 2207/20084; G06T 2207/10016;
(Continued)

(56) References Cited

U.S. PATENT DOCUMENTS

2018/0303466 A1 10/2018 Kashyap et al.
2018/0368818 A1* 12/2018 Oguri ...................... E03D 11/13
2020/0008786 A1* 1/2020 Sekine ................. A61B 5/6891

FOREIGN PATENT DOCUMENTS

JP 2017-96890 A 6/2017
JP 2017-137707 A 8/2017
(Continued)

OTHER PUBLICATIONS

Hachuel et al., Augmenting Gastrointestinal Health: A DeepLearning Approach to Human Stool Recognition and Characterization in Macroscopic Images, arxiv.org, Cornell University Library, 201 Olin Library Cornell University Ithaca, NY 14853, Mar. 25, 2019 (Mar. 25, 2019), XP081157875; (8 pages).
(Continued)

*Primary Examiner* — Zhitong Chen
(74) *Attorney, Agent, or Firm* — Morrison & Foerster LLP

(57) ABSTRACT

A determination device includes an acquisition unit configured to acquire image information of a target image in which excrement is captured and a determination unit configured to determine a characteristic of the excrement in the target image, select a part of the excrement specified according to a time series of excretion, and confirm a representing characteristic for representing the excrement.

17 Claims, 7 Drawing Sheets

(51) Int. Cl.
*G06V 10/764* (2022.01)
*E03D 9/00* (2006.01)

(52) U.S. Cl.
CPC ............... *G06T 2207/20081* (2013.01); *G06T 2207/20084* (2013.01); *G06V 2201/03* (2022.01)

(58) Field of Classification Search
CPC .. G06V 10/62; G06V 10/764; G06V 2201/03; E03D 9/00; A61B 10/0038; A61B 5/0033; A61B 5/0082; G01N 33/4833; G01N 21/85
See application file for complete search history.

(56) References Cited

FOREIGN PATENT DOCUMENTS

KR        101781996 B1 *   9/2017  ............... A61B 5/00
WO       2017/135169 A1     8/2017

OTHER PUBLICATIONS

Is Spasticity constipation [online], medical corporation ** meeting *—*, internal medicine clinic, Aug. 2016, [May 2, 2023 search], and Internet URL: https://kunichika-naika.com/information/hitori201608.
Konishi Muneaki, "[ Constipation ] By not coming out, **?", thing reliance [online] to stretch, The medical corporation association extensive blessing meeting The Haruyama surgical hospital, Jul. 2010, No. 19, [May 2, 2023 search], Internet URL: https://www.haruyama-hosp.com/wp/wp-content/themes/mcf/img/pdf/harunotayori19.pdf.
Notification of Reasons for Refusal dated May 16, 2023, directed to JP Application No. 2019-173484; 5 pages.

* cited by examiner

| Type | | |
|---|---|---|
| 1 |  | SEPARATE HARD LUMPY STOOLS LIKE NUTS (DIFFICULT TO PASS) |
| 2 |  | SAUSAGE-SHAPED MERGED HARD LUMPY STOOLS |
| 3 |  | SAUSAGE-SHAPED STOOLS WITH CRACKS ON SURFACE THEREOF |
| 4 |  | SAUSAGE-SHAPED, SMOOTH AND SOFT STOOLS |
| 5 |  | STOOLS IN SOFT BLOBS WITH CLEAR-CUT EDGES (EASY TO PASS) |
| 6 |  | MUSHY STOOLS IN FLUFFY PIECES WITH RAGGED EDGES |
| 7 |  | ENTIRELY WATERY STOOLS WITH NO SOLID PIECES |

DETERMINATION DEVICE

CROSS REFERENCE TO RELATED APPLICATIONS

This application is a national stage application under 35 USC 371 of International Application No. PCT/JP2020/035405, filed Sep. 18, 2020, which claims the priority of Japanese Application No. 2019-173484, filed Sep. 24, 2019, the entire contents of each priority application of which is incorporated herein by reference.

FIELD OF THE DISCLOSURE

The present disclosure relates to a determination device.

BACKGROUND OF THE DISCLOSURE

There is an attempt to understand a health condition from the excrement of the living body. For example, a technique for estimating the characteristic of the excrement from a plurality of captured still images by using a camera to photograph the falling excrement is disclosed (for example, see Patent Document 1).

Patent Document 1 Japanese Unexamined Patent Application, First Publication No. 2017-137707

SUMMARY OF THE DISCLOSURE

The above-mentioned Patent Document 1 discloses the technique for estimating each characteristic of the excrement with various characteristic. That is, it is possible to estimate various characteristic of excrement; however, it is not easy for the user to use since it is not known the characteristic of which part of the excrement should be used to determine the user's own health condition.

An object of the present disclosure is to provide a determination device capable of identifying a representative part of the excrement even there are various characteristic mixed in the excrement.

An aspect of the present disclosure is a determination device including an acquisition unit configured to acquire image information of a target image in which excrement is captured; and a determination unit configured to determine determination items regarding to the excrement in the target image, wherein the determination items are characteristic of the excrement, and in a case in which the excrement includes a plurality of parts determined to have different characteristic from each other, the determination unit is configured to select a part among the plurality of parts according to a time series of the excretion and confirm the characteristic of the selected part as a representing characteristic representing the excrement.

DETAILED DESCRIPTION OF THE DISCLOSURE

Figure 1:
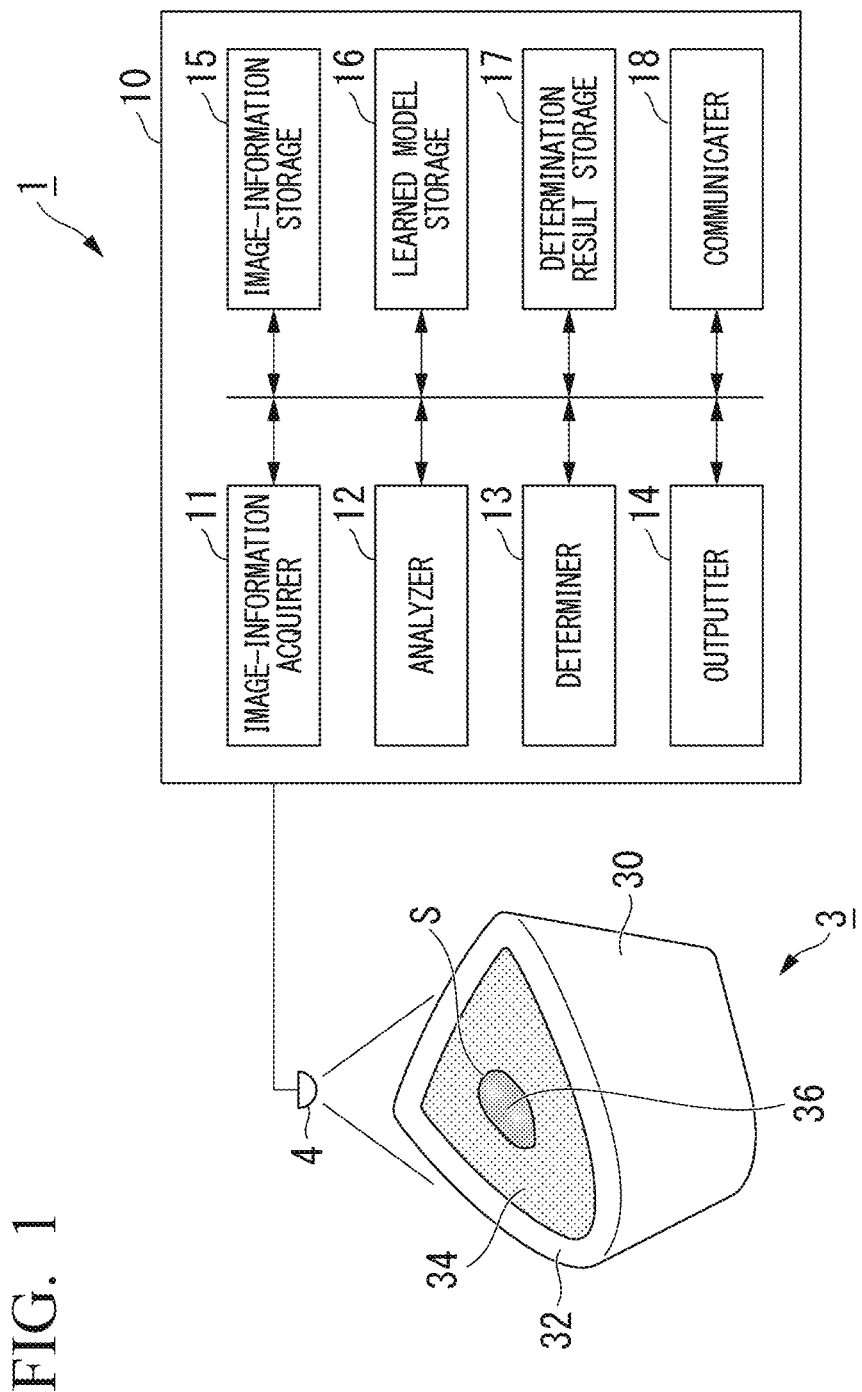
FIG. 1 is a block diagram showing a configuration of a determination system in which a determination device, according to some embodiments.

A determination system 1 according to some embodiments of the present disclosure includes, for example, a toilet device 3, an imaging device 4, and a determination device 10.

The toilet device 3 includes, for example, a toilet 30 having a toilet bowl 32. In the toilet device 3, a pooled water portion 36 is formed in an internal space 34 of the toilet bowl 32. The toilet device 3 is configured to be able to supply flush water S to the pooled water portion 36.

The imaging device 4 is provided at a position possible to image excrement. The imaging device 4 is installed on an upper side of the toilet bowl 30, for example, inside an edge on the rear side of the toilet bowl 32. The imaging device 4 is installed such that the lens are directed to a direction of the internal space 34 of the toilet bowl 32. That is, the imaging device 4 images the internal space 34 of the toilet bowl 32. Preferably, the imaging device 4 images the vicinity of the pooled water portion 36 of the toilet bowl 32, and images the stool that has fallen into the pooled water portion 36 and the stool that are falling. For example, the imaging device 4 images the vicinity of the pooled water portion 36 of the toilet bowl 32 based on instruction signals received from the determination device 10 and transmits image information of the captured images to the determination device 10.

The imaging device 4 repeatedly images the vicinity of the pooled water portion 36 of the toilet bowl 32 over time in the time series of the excretion. The imaging device 4 captures a plurality of images, for example, at the start, middle, and end of the excretion. As a result, the determination device 10 can analyze the images according to the captured time series, and the determination device 10 can determine the initially excreted stool, the intermediately excreted stool, and the last excreted stool.

In the following description, the imaging device 4 will be described using a case in which the imaging device 4 images the excrement that has fallen into the pooled water portion 36 of the toilet bowl 32 as an example. However, the present disclosure is not limited thereto. In the following description, the excrement may be referred to as the stool or the feces. For example, the imaging device 4 may be installed on the back side of the toilet seat so as to image the falling excrement from a side surface direction of the toilet bowl 32. The images captured by the imaging device 4 may be a moving image or a still image.

The determination device 10 includes, for example, an image-information acquisition unit 11, an analysis unit 12, a determination unit 13, an output unit 14, an image-information storage unit 15, a learned model storage unit 16, and a determination result storage unit 17. The image-information acquisition unit 11 is an example of the "acquisition unit". The analysis unit 12 is an example of an "estimation unit".

The image-information acquisition unit 11 acquires the image information of the images captured in the vicinity of the pooled water portion 36 of the toilet bowl 32. In the following description, an image captured in the vicinity of the pooled water portion 36 of the toilet bowl 32 may be referred to as a target image. The image-information acquisition unit 11 outputs the acquired image information to the analysis unit 12. The image-information acquisition unit 11 stores the acquired image information in the image-information storage unit 15.

The analysis unit 12 analyzes the images based on the image information acquired from the image-information acquisition unit 11. In the following description, the image to be analyzed may be referred to as a target image. The analysis by the analysis unit 12 is to estimate the items of determination regarding the excrement based on the image related to the excretion. In the following description, the item of determination regarding the excrement may be referred to as a determination item. The determination item may be at least related to the excrement, for example, the characteristic and amount of stool. The characteristic of the excrement includes the shape and color of the excrement. The amount of excrement includes the size of the excrement.

Figure 8:
FIG. 8 is a view showing examples of the characteristic of the excrement, according to some embodiments.
Figure 8:
Figure 8:
Figure 8:
Figure 8:
Figure 8:
Figure 8:

As shown in the example of FIG. 8, the characteristic of the stool can be divided into 7 categories based on the Bristol scale. The Bristol scale indicates the characteristic and condition of the stool and is an international stool classification index. The Bristol scale is often used in the medical field, for example. According to the Bristol scale, it is classified into type 1 to type 7 according to the amount of water contained in stool, that is, the amount of the fecal water content. The fecal water content of the healthy stool is the type 4. The fecal water content is lower as the Bristol scale type number becomes smaller, and the fecal water content is higher as the Bristol scale type number becomes larger. A range from the type 3 to the type 5 is a healthy range, the type 1 and the type 2 indicate the constipated stools, and the type 6 and the type 7 indicate the diarrheal stools.

The analysis unit 12 estimates the determination items using, for example, a learned model that has learned the contents corresponding to the determination items of the determination unit 13. The learned model is, for example, a model stored in the learned model storage unit 16. The learned model, for example, is a model learned using a data set in which the image in which the excrement is captured, that is, a learning image and a determination result for a determination item of the excrement captured in the learning image are associated with each other as teacher data. According to the learning, the learned model can output the determination result of the determination item in the input image as an estimated value.

The learned model is created using, for example, a deep learning method. In the following description, deep learning is abbreviated as DL. DL is a machine learning method using a deep neural network configured of a multi-layer neural network. In the following description, the deep neural network is abbreviated as DNN. DNN is realized by a network inspired by the principle of predictive coding in neuroscience, and is constructed by a function that mimics the neurotransmission network. However, the learned model is not limited to DNN. The learned model may be at least a model that has learned the correspondence relationship between the image and the determination result.

The determination unit 13 determines the determination items in the excrement imaged in the target image by using the analysis result acquired from the analysis unit 12. In the following description, the analysis result acquired from the analysis unit 12 may be referred to as an estimation result.

In general, the characteristic of stool may change over time in the process of one time of the excretion. For example, at the beginning of excretion, there may be separate hard lumps type stools, for example, stools classified as type 1 according to the Bristol scale, and finally, watery stools, for example, stools classified as type 7 may be excreted.

Changes in the stool characteristic cannot be understood correctly unless the person has very high stool health literacy. For example, as described above, if the type 1 stool is excreted initially and the type 7 stool is excreted at last, the medically correct interpretation is that the "initially excreted stool" represents the excrement. In other words, the separate hard lumps type stools are the representative of the excrement state and are interpreted as being constipated. A general user with no medical knowledge and low health literacy regarding the stools may misinterpret that the "last excreted stool" is the stool representing his or her original excrement state. In such cases, there is a risk of taking antidiarrheal drugs, that is, the drugs for stopping the diarrhea due to wrong self-judgment and further worsening the constipation.

The reason why the "initially excreted stool" should be interpreted to represent the excrement will be additionally descripted. The large intestine is an organ located between the small intestine and the anus. The large intestine is composed of the cecum, the ascending colon, the transverse colon, the descending colon, the sigmoid colon, and the rectum in a sequence from the small intestine to the anus. Under the normal conditions, when the user does not feel the defecation desire, there is no stool in the rectum and the stool is stored from the descending colon to the sigmoid colon. When the stored stool comes down to the rectum at once due to the peristaltic movement of the intestine, the user feels the defecation desire and defecates. Since the water in the stool is absorbed as the stool passes through the large intestine, the stool that comes out later is interpreted as the back stool, and the "stool from the descending to the sigmoid colon" that should be originally stored can be regarded as the essence for best reflecting the healthy state of the user.

Based on such an interpretation, in some embodiments, the characteristic of the stool is determined on behalf of the stool that can be regarded as the essence. A specific method for the determination unit 13 to determine the characteristic of the stool will be described in details later.

The output unit 14 outputs the determination result by the determination unit 13. The output unit 14, for example, may be configured to transmit the determination result to the terminal of the user who has performed the excretion behavior. Accordingly, it is possible for the user to recognize the determination result of the characteristic and amount of excrement. The image-information storage unit 15 stores the image information acquired by the image-information acquisition unit 11. The learned model storage unit 16 stores the learned model corresponding to each of the determination items. The determination result storage unit 17 stores the determination result by the determination unit 13. The communication unit 18 communicates with the toilet device 3, the imaging device 4, or an external device (not shown). For example, in a case in which, operations such as sitting or unseat by the user of the toilet device 3, starting to use local cleaning, and cleaning the toilet bowl 32 after excretion are detected by a function unit (not shown) provided in the toilet bowl 30, the communication unit 18 receives the detection result from the toilet device 3. The communication unit 18 transmits control information indicating an imaging instruction to the imaging device 4.

Figure 2:
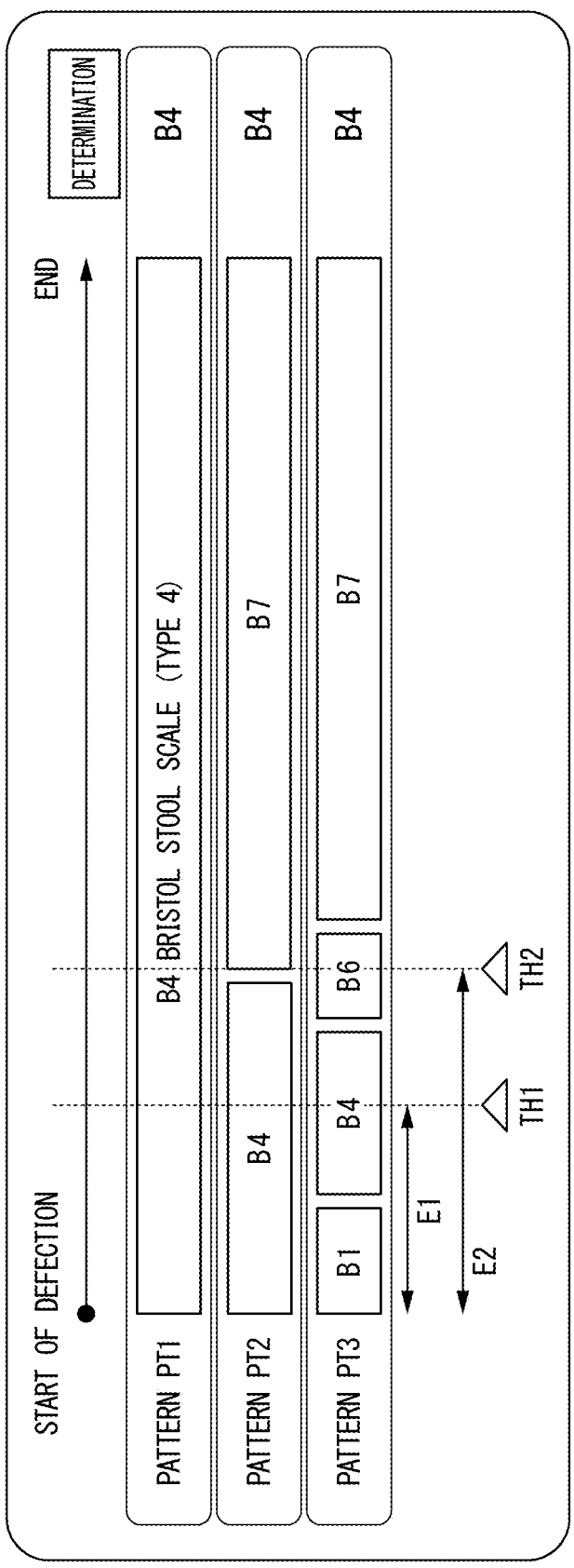
FIG. 2 is a view showing a processing of a determination unit, according to some embodiments.

A specific method for the determination unit 13 to determine the characteristic of the stool will be described with reference to FIG. 2. The horizontal axis in FIG. 2 is the time axis from the start of excretion, that is, from the start of the defecation to the end of defecation. In FIG. 2, the result determined by the determination unit 13 is shown along the time axis.

As shown in pattern PT1 of FIG. 2, a case in which the stool has the same characteristic from the start of defecation to the end of defecation is excreted will be considered. In this case, since the characteristic of the excrement from the start of defecation to the end of defecation is no changed, the determination unit 13 determines the detected characteristic as the characteristic representing the excrement. In the example of the pattern PT1, the characteristic of the excrement is type 4.

As shown in patterns PT2 and PT3 of FIG. 2, a case in which a small amount of stool compared to the total amount is excreted at the start of defecation, and then a large amount of stool having characteristic different from the initial stool is excreted will be considered.

In this case, if the initial stool is not in an extremely small amount, the determination unit 13 determines the characteristic of the initially excreted stool as a characteristic representing the excrement.

Specifically, the determination unit 13 determines predetermined ratios H1 and H2 with respect to the total amount of excrement in advance. The ratio H1 is a ratio corresponding to a threshold value TH1 for determining whether or not the amount of the initially excreted stool is small. The ratio H1 may be set to any ratio. The ratio H1 is, for example, from zero to less than 50%, preferably equal to or less than 30%. The ratio H2 is a ratio corresponding to a threshold value TH2 for determining the region of stool that can be regarded as the essence. The ratio H2 may be set to any ratio. The ratio H2 is, for example, around 50%.

The determination unit 13 first determines the total amount of excretion. The method for determining the total amount of excretion will be described in details later. The determination unit 13 calculates an amount of stool E1 that occupies the predetermined ratio H1 determined above based on the determined total amount. The determination unit 13 calculates the amount of stool E2 that occupies the predetermined ratio H2 determined above based on the determined total amount.

The determination unit 13 compares the amount of initially excreted stool with the calculated amount of stool E1. As shown in the pattern PT2, in the case in which the amount of the initially excreted stool is larger than the predetermined amount E1, the determination unit 13 confirms the determination result of using the characteristic of the initially excreted stool as the characteristic representing the excrement. In the example of this pattern PT2, since the amount of initially excreted stool is larger than the amount E1, the determination unit 13 confirms the characteristic B4, which is the characteristic of the initially excreted stool, as the characteristic of excrement.

As shown in the pattern PT3, when the amount of initially excreted stool is smaller than the predetermined amount E1, the determination unit 13 extracts the stool from the start of defecation until the predetermined amount E2 is excreted. The determination unit 13 determines the characteristic of the extracted stool, and confirms the characteristic of the stool having the largest amount among the determined characteristic as the characteristic representing excrement. In the example of pattern PT3, since the amount of initially excreted stool is smaller than the amount E1, the determination unit 13 confirms the characteristic B4, which is the characteristic of the secondary excreted stool with the largest amount of stool among the characteristic of B1, B4, and B6 of the stools excreted from the start of defecation to the amount E2, as the characteristic of excrement.

Figure 3:
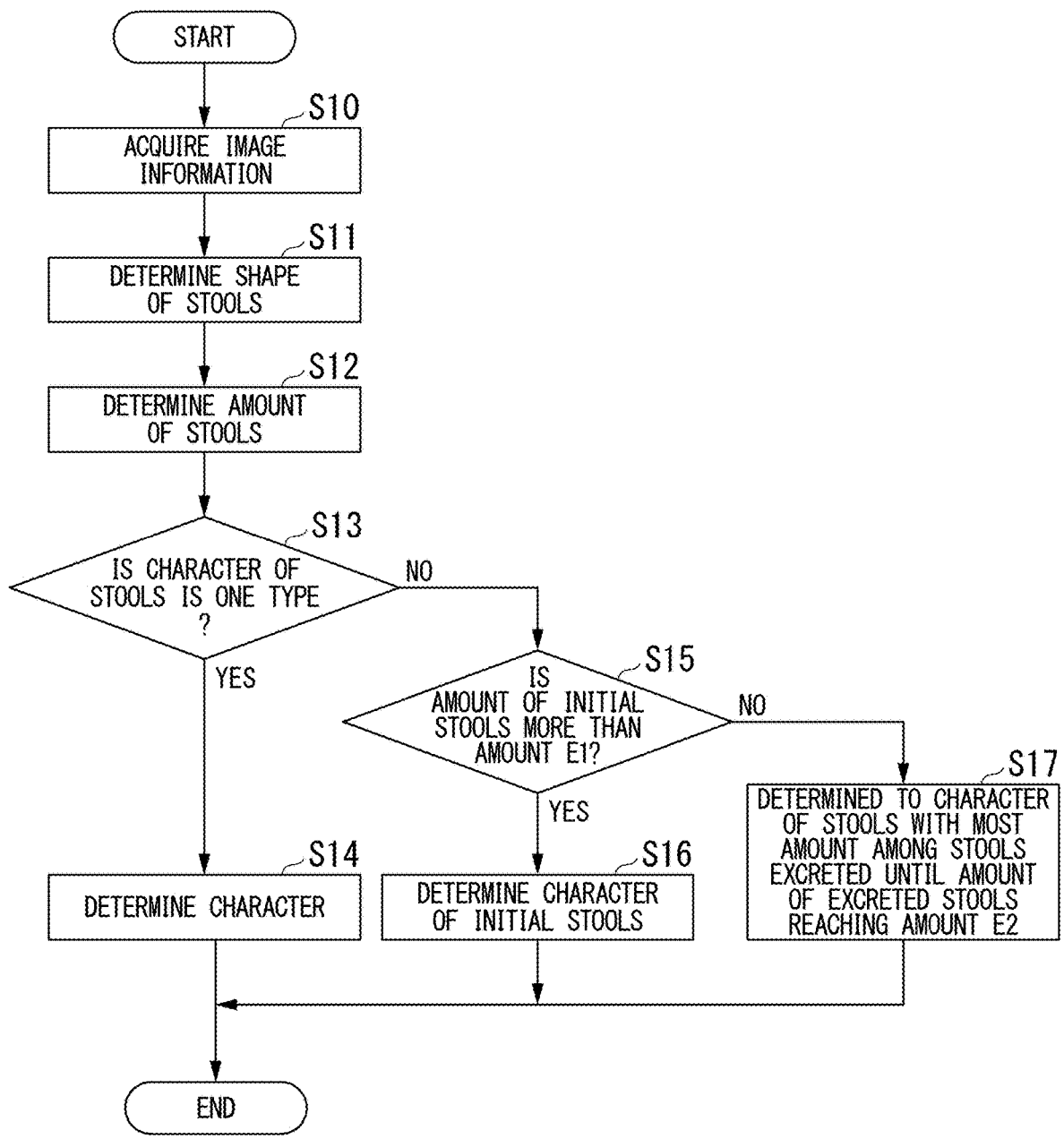
FIG. 3 is a flowchart showing a processing flow of the determination unit, according to some embodiments.

The flow of processing performed by the determination device 10 according to some embodiments will be described with reference to FIG. 3. The determination device 10 acquires image information by the image-information acquisition unit 11 (step S10). The determination unit 13 determines the characteristic of the stool for each target image based on the image information (step S11), and determines the amount of the stool (step S12). In a case in which the excrement having mixed different characteristic are captured in the target image, the determination unit 13 determines the characteristic for each imaging region of the excrement.

The determination unit 13 uses, for example, an estimation result obtained by making the analysis unit 12 to estimate the characteristic of the stool as the determination result. In this case, the analysis unit 12 outputs the estimation result obtained by inputting the image information to the learned model to the determination unit 13. The learned model stores, for example, a data set in which a learning image in which the excrement is captured and a result of determining the characteristic and amount of excrement in the learning image are associated with each other as the teacher data. The learned model is a model learned to output the result of determining the characteristic and amount of excrement in the input image by comparing with the teacher data.

The determination unit 13 determines the characteristic of the stool. The determination unit 13 determines whether or not the characteristic of the stool captured in the target image is not changed, that is, whether or not there is only one type of characteristic (step S13). In a case in which the characteristic of the excrement is one type, the determination unit 13 confirms the result of determining the characteristic of the only one type as the determination result of the characteristic representing the excrement (step S14). On the other hand, in a case in which when the characteristic of the excrement is not one type, that is, there are a plurality of types of excrement, the determination unit 13 determines whether or not the amount of initially excreted stool is larger than the predetermined amount E1 (step S15). The amount E1 is an amount that occupies a predetermined ratio H1 with respect to a representative amount of excrement.

When the amount of the initially excreted stool is larger than the amount E1, the determination unit 13 confirms the characteristic of the initially excreted stool as the result of determining the characteristic representing the excrement (step S16). On the other hand, in a case in which the amount of initially excreted stool is smaller than the amount E1, the determination unit 13 extracts the stool from the start of excretion until the amount E2 is excreted. The amount E2 is an amount that occupies a predetermined ratio H2 with respect to a representative amount of excrement. The determination unit 13 determines the characteristic of the extracted stool. The determination unit 13 confirms the result of determining the characteristic of the stool having the largest amount among the determined characteristic as the characteristic representing the excrement (step S17).

As described above, the determination device 10 according to some embodiments includes an image-information acquisition unit 11 and a determination unit 13. The image-information acquisition unit 11 acquires the image information of the target image in which the excrement is captured. The determination unit 13 determines determination items relating to the excrement in the target image. The determination item regarding the excrement is the characteristic of the excrement. The determination unit 13 selects a part of the excrement specified based on the time series of excretion, and determines the characteristic of the selected portion as the characteristic representing the excrement, that is, as a representative characteristic of the excrement.

As a result, it is possible for the determination device 10 according to some embodiments to select a part that is considered to represent the user's defecation based on the time series of excretion, and to specify the characteristic of the selected part representing the excrement. Therefore, it is possible to present an index that is easy for the user to understand, such as presenting one characteristic that is considered to be the most representative of defecation, and accordingly it is possible to improve convenience.

According to some embodiments, the determination items related to excrement are the characteristic and amount of excrement. In a case in which the excrement contains a plurality of parts having different characteristic from each other and when it is determined that the amount of the initially excreted stool (first part) among the plurality of parts is larger than a threshold value TH1 corresponding to the predetermined amount E1, that is, a first threshold value, the determination unit 13 determines that the characteristic of the initially excreted stool, that is, the characteristic of the first part of the stool as the characteristic representing the excrement. The predetermined amount E1 is the ratio H1 of the total amount, that is, the amount corresponding to the first ratio. Accordingly, it is possible to determine the characteristic that is considered to be the most representative of defecation as the characteristic of excrement by a simple method in which the amount of the initially excreted stool is compared with the predetermined amount E1.

According to some embodiments, in a case in which it is determined that the amount of the initially excreted stool, that is, the amount of the first part of the stool, is equal to or less than the threshold TH1 corresponding to the predetermined amount E1, the determination unit 13 confirms the characteristic of the stool that is determined to have the largest amount, that is, the characteristic of the third part of the stool, among the stools (second part) excreted from the start of excretion to the total amount ratio H2, that is, until the amount of the second ratio is excreted, as the characteristic representing the excrement. As a result, in which the amount of initially excreted stool is extremely small, it is possible for the determination unit 13 to determine the characteristic that is considered to represent the most stool among the later stools to be considered to represent the excrement as compared with the initial excreted stool as the characteristic of excrement.

According to the described above, the case in which the determination unit 13 determines the characteristic and amount of stool based on the estimation result by the analysis unit 12 has been described as an example. The present disclosure is not limited to this example. For example, the determination unit 13 may determine the characteristic and amount of stool by using a conventional image analysis method such as image color and edge detection without using the estimation result of the analysis unit 12. In this case, the analysis unit 12 can be omitted.

In some embodiments, the determination device 10 determines the characteristic representing the excrement without using the time series information.

Due to the characteristic of the human body, the water contained in the stool is absorbed as passing through the large intestine. Therefore, the initially excreted stool tends to have a relatively small amount of water and become harder than the initially excreted stool, and the stool excreted later tends to have a large amount of water to be soft. At the extreme, the stools tend to be excreted in an ascending order of type number on the Bristol scale. However, the type of the Bristol scale in the initial excreted stool varies depending on the excretion and is not particularly determined.

Utilizing such a characteristic in some embodiments, in a case in which the excrement contains a plurality of parts determined to have different characteristic from each other, the determination unit 13 confirms the characteristic with the smallest type number on the Bristol scale as the characteristic representing. As a result, it is possible for the determination unit 13 to select the characteristic of the initially excreted part without distinguishing between the initially excreted part and the last excreted part.

As described above, the determination device 10 according to the present modification example of some embodiments includes an image-information acquisition unit 11 and a determination unit 13. The image-information acquisition unit 11 acquires the image information of the target image in which the excrement is captured. The determination unit 13 determines a determination item relating to excrement in the target image. The determination item regarding the excrement is the type number on the Bristol scale, which is an example of the characteristic of excrement classified according to the amount of water contained in the excrement. In a case in which the excrement contains a plurality of parts determined to have different characteristic from each other, the determination unit 13 determines the characteristic having the smallest type number on the Bristol scale as the characteristic representing the excrement. The characteristic with the smallest type number on the Bristol scale is an example of "the characteristic of the part determined to be in the category with the lowest water content". As a result, it is possible for the determination device 10 to select the characteristic of the initially excreted part of the excrement that is considered to reflect the health condition most by extracting the smallest number of the type on the Bristol scale determined with respect to the excrement.

In some embodiments, the determination device 10 determines the amount of excrement based on the target image.

Figure 4:
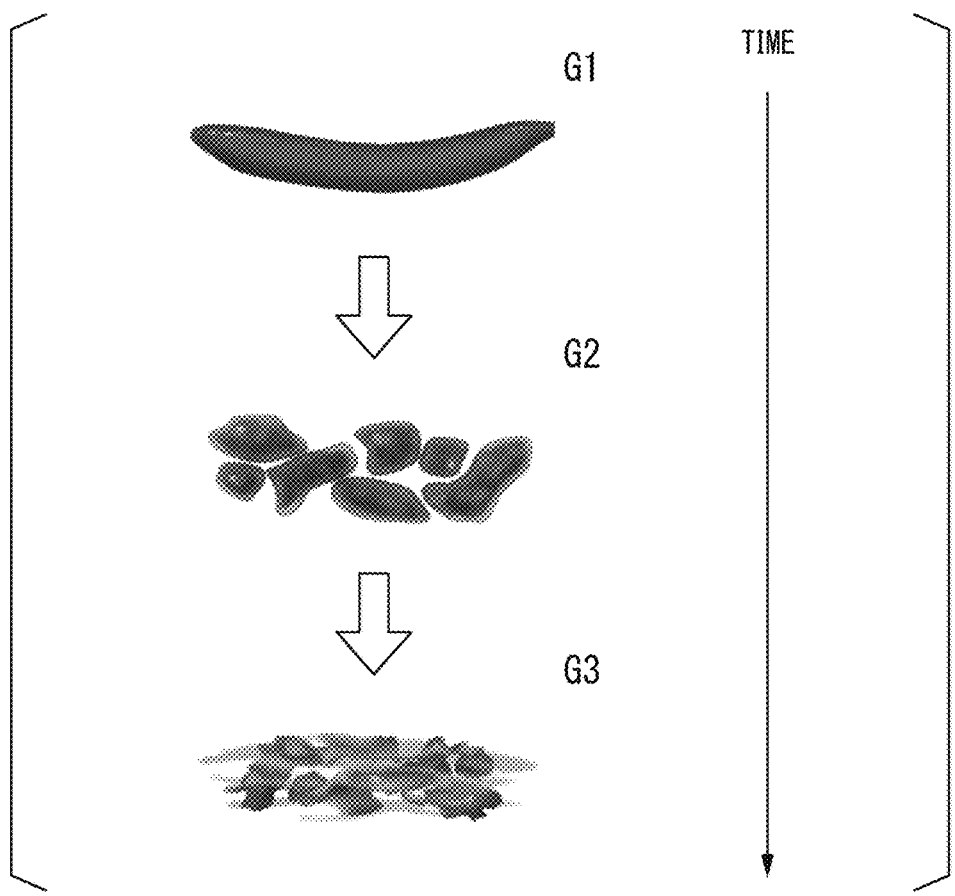
FIG. 4 is a view showing a processing of a determination unit, according to some embodiments.

As shown in FIG. 4, the stool falls into the pooled water portion 36 in the toilet bowl 32 and dissolves, or is affected by urine and human's bottom flushing water such that the characteristic and amount thereof change over time. In such an example, in the target image G1 immediately after the excretion, the banana-shaped stool classified into Bristol scale type B4 changes as shown in the target images G2 and G3 with the passage of time. In the target image G2, the stool is soggy and the shape is broken. In the target image G3, the stool is dissolved in water. In this manner, the shape of stool changes over time. In this case, it is considered to lead to a mistaken determination by determining the characteristic of the stool that was originally type B4 based on the target images G2 and G3.

As a countermeasure against such a mistaken determination, in some embodiments, the determination unit 13 extracts only an image such as the target image G1 that can be used to accurately determine the characteristic of the stool, and the images such as images G2 and G3 cannot be used to accurately determine the characteristic of the stool are excluded. Specifically, the determination unit 13 determines the determination item for an image as a target before the state of the stool is changed when the stool collapses or melts.

Figure 5:
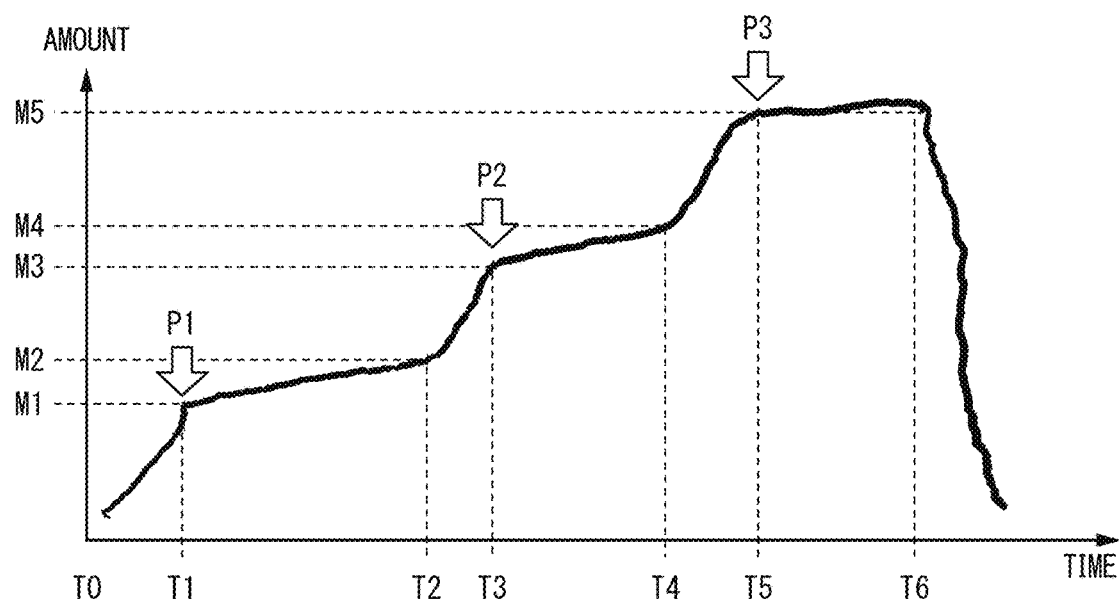
FIG. 5 is a view showing the processing of a determination unit, according to some embodiments.

The process performed by the determination unit 13 according to some embodiments will be described with reference to FIG. 5. FIG. 5 is a graph showing the correspondence relationship between time and the amount of stool. In FIG. 5, the horizontal axis represents the time and the vertical axis represents the amount.

The determination unit 13 derives the correspondence relationship between the time and the amount of stool as shown in FIG. 5 based on the result of determining the amount of stool. In the example shown in FIG. 5, the time-dependent change of the amount of stool is shown when the amount M5 is excreted between the time T0 and the time T6. The slope between time T0 to time T1, time T2 to time T3, and time T4 to time T5 is relatively steep, while the slope between time T1 to time T2 and time T3 to time T4 is relatively gentle. It is because the excrement falls during the period when the slope is steep (time T0 to time T1, time T2 to time T3, time T4 to time T5), and during the time when the slope is gentle (time T1 to time T2, time T3 to time T4), the excrement that has fallen collapses and melts such that it is considered that the amount of stools seems to have increased slightly.

According to such consideration, it is considered that the characteristic of the stool can be accurately determined from the image captured at the time when the slope is steep. It is considered that the characteristic of the stool cannot be accurately determined from the image captured at the time when the slope is gentle. Among the images captured during the period when the slope is steep, the images captured during the period when the slope does not change is an image in which the excrement is falling. Therefore, it is considered to be too early to determine the characteristic and amount. That is, the image captured at the time when the slope changes from a steep state to a gentle state is the most suitable image for determining the characteristic and amount of stool. The determination unit 13 extracts such an image.

Specifically, the determination unit 13 calculates the time-dependent change rate of the amount of stool from the relationship between the time when the image is captured and the amount of stool determined in the image. The determination unit 13 classifies the time-dependent change rate into either of two categories, for example, steep and gentle, by comparing the time-dependent change rate with a predetermined threshold value K. The determination unit 13 extracts the captured image at the time when the two categories are switched and at the time when the two categories are switched from steep to gentle.

In the example in FIG. 5, point P1 (T1, M1), point P2 (T3, M3), and point P3 (T5, M5) are points where the slope changes from steep to gentle. The determination unit 13 extracts the images captured at the time point T1, time point T3, and time point T5 corresponding to these points as images capable of determining the characteristic and amount of stool with the highest accuracy.

Figure 6:
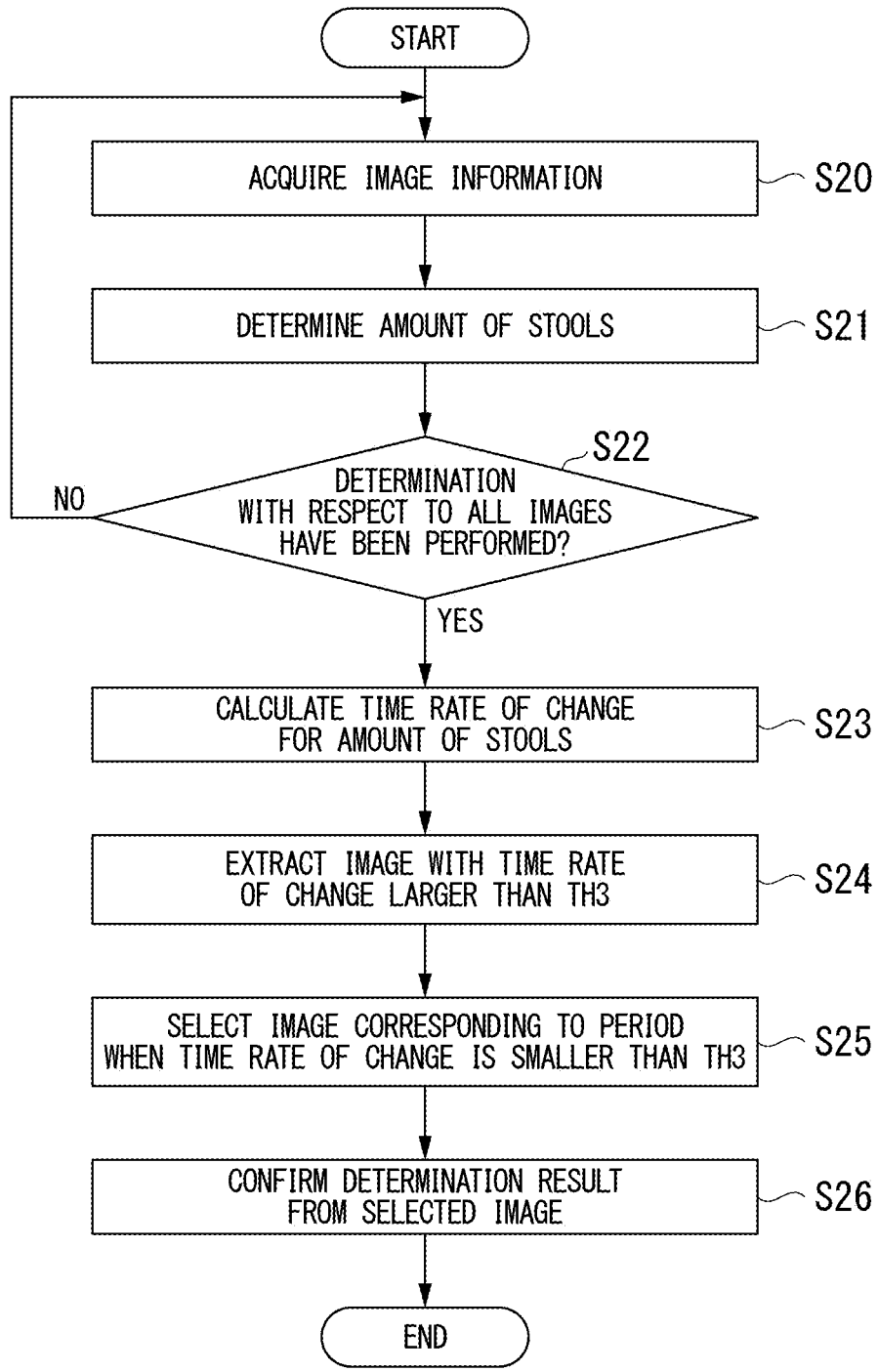
FIG. 6 is a flowchart showing a processing flow of the determination unit, according to some embodiments.

The flow of processing performed by the determination device 10 according to some embodiments will be described with reference to FIG. 6. Since step S20 and step S21 shown in FIG. 6 are the same processes as step S10 and step S11 in FIG. 4, the description thereof will be omitted.

The determination unit 13 determines whether or not the amount of stool has been determined for all of the target images, and in a case in which there is an image in which determination has not yet been performed, the determination unit 13 returns to step S20 and repeats the process of determining the amount of stool in the undetermined image (step S22). The determination unit 13 calculates the time-dependent change rage, for example, the slope. The determination unit 13 calculates the time-dependent change rate in the amount of stool from the relationship between the imaging time in the target image and the amount of stool determined from the image (step 23). The determination unit 13 extracts an image captured at a time when the time-dependent change rate in the amount of stool is larger than a predetermined threshold value TH3, for example, a slope K (step S24). The determination unit 13 selects an image corresponding to the time when the time-dependent change rate changes to a value smaller than the threshold value TH3 among the extracted images (step S25). The determination unit 13 determines the characteristic and amount representing the stool using the determination result of the selected image (step S26).

As described above, in the determination device 10 according to some embodiments, the target images are a plurality of images of the internal space 34 of the toilet bowl 32 in excretion, for example, the vicinity of the pooled water portion 36 which are repeatedly imaged in chronological sequence. The determination items regarding the excrement are the characteristic and amount of excrement. The determination unit 13 extracts a target image in which the time-dependent change rate in the amount of excrement is larger than the predetermined slope K regarding the relation between the imaging time of each target image and the amount of excrement. The predetermined slope K as the time-dependent change rate of the amount of excrement is an example of the "second threshold value". The determination unit 13 determines the characteristic and amount representing the excrement based on the characteristic and amount of excrement determined in the extracted target image. As a result, it is possible for the determination device 10 to determine the characteristic and amount of stool based on the image in which the state before the excrement collapses or melts is captured. It is possible for the determination device 10 to accurately determine the characteristic and amount of excrement.

In some embodiments, the determination unit 13 adopts the determination result when the chronologically determined results of the characteristic are the same over a plurality of times.

Figure 7:
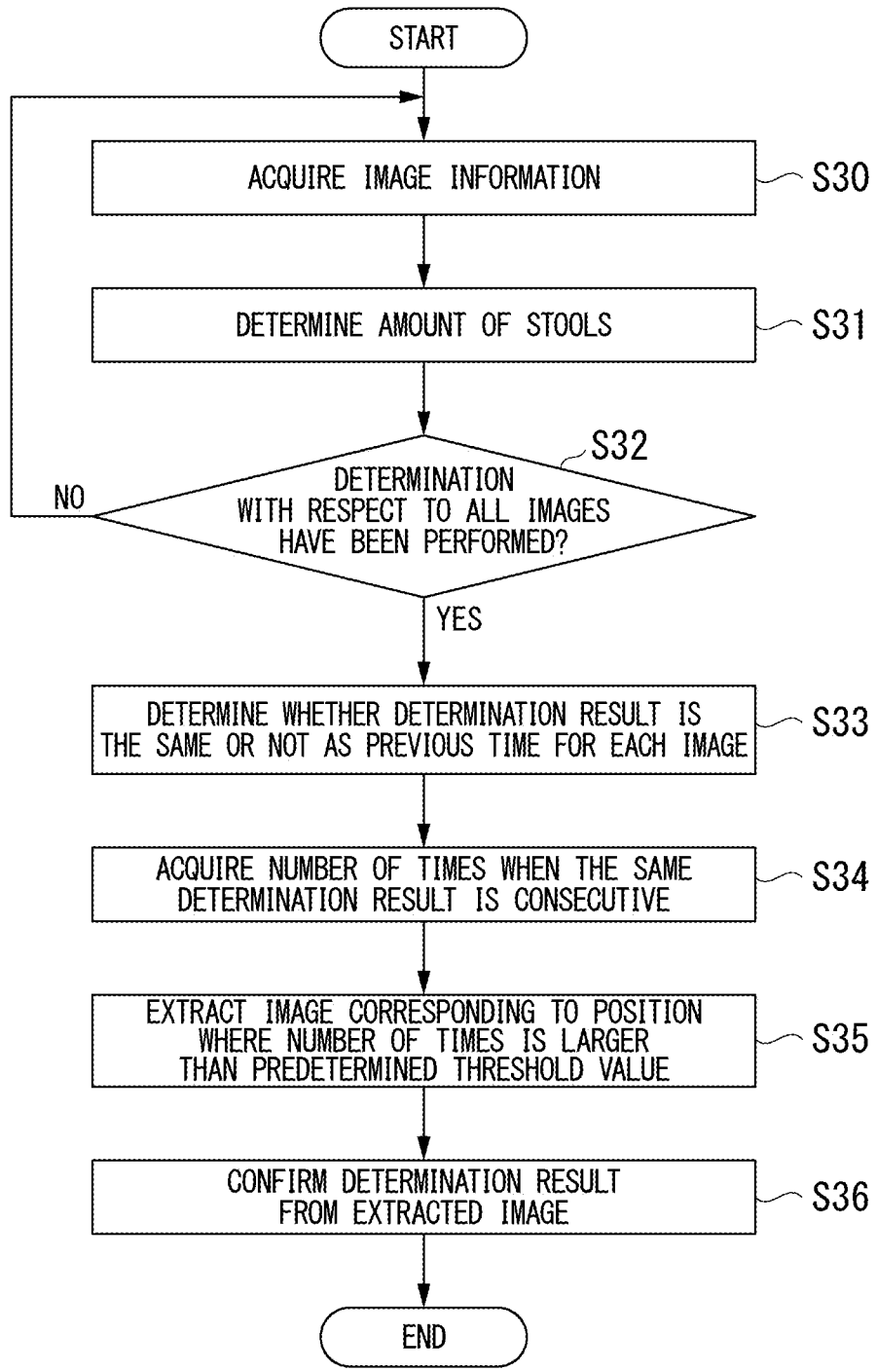
FIG. 7 a flowchart showing the processing flow of the determination unit, according to some embodiments.

The flow of processing performed by the determination device 10 according to some embodiments will be described with reference to FIG. 7. Since step S30 to step S32 of FIG. 7 are the same with step S20 to step S22 of FIG. 6, the description thereof will be omitted.

The determination unit 13 determines whether or not the same determination result as the previous time is obtained for each image (step S33). The determination unit 13 acquires the number of times that the same determination result is consecutive (step S34). The determination unit 13 extracts an image corresponding to a location where the number of acquired number of times is larger than a predetermined threshold value (step S35). The determination unit 13 determines the characteristic and amount representing the stool using the determination result of the extracted image (step S36).

As mentioned above, the characteristic and amount of stool change over the process of excretion. The shape of the stool may be collapsed due to the impact of being dropped on the toilet bowl, or the characteristic and amount of the stool may change over time due to the effect of the stool dissolving in the water. Urination may occur before, after, or at the same time as the defecation. Even if the method according to the embodiment described above is adopted, it is possible that the slope cannot be clearly divided into two categories, that is, steep or gentle.

In some embodiments, it is noted that the characteristic of stool do not change so much during the excretion; however, the characteristic of stool continuously changes over time after falling. Utilizing the present characteristic, the determination unit 13 determines that the stool is not a stool that collapses after falling when the determination results of the characteristic are the same for a plurality of times F1 over time. The determination unit 13 determines that the characteristic of the stool that is not the stool that collapses after falling should be the original characteristic of the excrement, and confirms the characteristic.

As described above, in the determination device 10 according to the first modification example of some embodiments, the target image in which the number of consecutive times that the determination results according to the imaging time of each target image are the same is larger than the plurality of times F1 is extracted. The plurality of times F1 is an example of a "third threshold". The determination unit 13 determines the characteristic representing the stool based on the characteristic of the stool determined in the extracted target image. As a result, even when the slope cannot be clearly classified as steep or gentle, it is possible for the determination unit 13 to extract an image the stool that is not the stool collapsed after falling is captured and to confirm the characteristic and the amount representing the excrement accurately.

In some embodiments, the determination unit 13 determines that the amount of stool determined to be the largest amount over time represents the amount of the excrement. The amount of stool that is totally excreted is the most probable amount of stool. Even if the maximum amount is suddenly determined at a time considered to be in the middle of excretion, such as time T3 as shown in FIG. 5, the determination unit 13 regards the determination of the maximum amount as the mistaken determination since it is considerable that the excretion is in the middle over time. The determination unit 13 determines the amount corresponding to the end of excretion over time and determined to be the largest amount over time as the amount of the excrement. The determination unit 13 determines the maximum amount of excrement at a time considered to be the last of excretion, for example, at time T6 in FIG. 5.

As described above, in some embodiments, the determination item regarding excrement is the amount of excrement. The determination unit 13 confirms the amount corresponding to the end of excretion over time and determined to be the largest amount among the amount of excrement determined in each target image as the amount of the excrement. Accordingly, even if the maximum amount is suddenly determined since there is noise in the image during excretion, it is possible for the determination unit 13 to recognize the determination as a mistaken determination, and to prevent the accuracy of the determination from being deteriorated.

In some embodiments, when the determination results of the amount of stool over time match for a plurality of times, the determination unit 13 adopts the determination results.

In some embodiments, the characteristic that the amount of stool increases during excretion, the amount of stool after falling increases slightly, and the amount does not increase immediately after the stool that has been totally excreted. Utilizing such a characteristic, in a case in which the determination results of the amount of stool over time are the same for a plurality of times F2, the determination unit 13 determines that the stool is neither the stool in the middle of excretion nor the stool collapsing after falling, and the determination unit 13 determines that the stool corresponds to the stool immediately after the end of excretion. The determination unit 13 confirms the amount of stool determined to be the stool immediately after the end of excretion as the amount of excrement. The plurality of times F2 is an example of a "fourth threshold".

As described above, in the determination device 10 according to the third modification example of some embodiments, the target image in which the number of times that the determination results according to the imaging time of each target image are consecutively the same result is larger than the plurality of times F2, is extracted. The determination unit 13 determines the amount representing the excrement, that is, the representing amount of the excrement, based on the amount of excrement determined in the extracted target image. As a result, even when the slope cannot be clearly classified as steep or gentle, it is possible for the determination unit 13 to extract the image of stool that is not the stool collapsed after falling so as to confirm the characteristic and amount representing the excrement accurately.

In some embodiments, the determination unit 13 determines the characteristic of the stool based on a combination of the determination results determined by using a plurality of indexes.

The Bristol scale is an international stool classification index and is widely used in the medical field. If it is possible to classify the stool correctly according to the present index, it is possible to make an accurate determination. However, actually, it was often classified subjectively according to experience and sensation. In particular, the type 1, type 4, and type 7 can be correctly classified when they are classified by inexperienced operators. On the other hand, it is difficult for the operators to distinguish between the types classified therebetween, for example, between the type 2 and type 3, and type 5 and type 6, and the determination tends to vary.

According to some embodiments, the determination device 10 determines each of a plurality of indexes of excrement, and quantitatively determines the characteristic of stool by combining the determination results. Specifically, the determination unit 13 determines the characteristic of the excrement based on the combination of the results of determining the texture, continuity, and edge of the excrement. The texture is a sensation of appearance on the surface of excrement, and is a degree corresponding to, for example, a sensation of separate hard lumps, banana, and the like. The continuity is the connection of excrement, for example, the degree of connection or break. The edge is the contour of the excrement, for example, the degree of sharpness or blurring.

As described above, in the determination device 10 of some embodiments, the determination unit 13 determines the characteristic of the excrement based on the combination of the results of determining the texture, continuity, and edge of the excrement. As a result, the determination device 10 can quantitatively and objectively determine the characteristic so as to reduce the variation in the determination and make the determination to be with high accuracy.

The determination device 10 according to some embodiments can also be applied to the creation of the teacher data. In a case of determining or estimating the characteristic of stool using the learned model, the accuracy of the teacher data greatly affects the accuracy of the estimation. That is, the learned model that has learned the teacher data including the variation in the determination may lead to a mistaken determination in the classifications such as type 2 and type 3 as same in the teacher data. In such a case, if the determination device 10 quantitatively determines the characteristic of the learning image based on a plurality of indexes, it is possible to generate the high-quality teacher data with reduced variation in the determination. A learned model that has learned the high-quality teacher data is able to accurately determine the characteristic of stool even if the characteristic are near the boundary between type B2 and type B3.

The whole or part of the process performed by the determination device 10 according to the embodiments described above may be realized by a computer. In this case, a program for realizing such functions may be recorded in a computer-readable recording medium as a program, and the processing described above is performed when the program is read by the computer and executed by the computer. The "computer system" refers to a system including an operating system (OS) and hardware such as peripheral devices. The "computer-readable recording medium" refers to a removable medium such as a flexible disk, a magneto-optical disk, a read-only memory (ROM), and a compact disk read-only memory (CD-ROM), and a storage such as a hard disk disposed inside the computer system. Furthermore, in a case that the program is transferred through a network such as the internet and a communication line such as the telephone line, the "computer-readable recording medium" may refer to the communication line that is configured to maintain the program temporarily and dynamically, or the "computer-readable recording medium" may refer to the device configured to maintain the program for a certain period such as a volatile memory inside the computer system used as a server or a client. The program may be a program for realizing part of the functions described above, the program may be combined with the program recorded in the computer system to realize the functions, and the program may be realized by using a programmable logical device such as a field-programmable gate array and the like.

The specific configuration of the determination device according to the present disclosure is not limited to the embodiments. Each configuration described in the above-described embodiments and modifications is only an example, and various changes in the structure are possible without departing from the spirit of the present disclosure.

According to each of the embodiments and modifications of the present disclosure shown above, it is possible to provide a determination device capable of identifying a representative portion even in excrement in which various characteristic are mixed.

The invention claimed is:

1. A determination device comprising a computer configured to:
   acquire image information of a target image in which excrement is captured;
   determine a type of the excrement in the target image;
   select a part of the excrement specified based on a time series of excretion; and
   confirm a representing type for representing a total amount of the excrement by:
   determining the total amount of the excrement; and
   in a case in which a plurality of the parts having different types are included in the excrement, and when an amount of a first part being initially excreted among the plurality of parts having a first type is determined to be larger than a first type threshold corresponding to a first ratio of the amount of the initially excreted excrement having the first type to the total amount of the excrement, confirm the type of the initially excreted excrement as the representing type of the total amount of the excrement.

2. The determination device of claim 1, wherein in a case in which the amount of the first part is determined to be equal to or less than the first type threshold, the computer is configured to determine a type of a third part determined to have the most amount among a second part excreted from starting of the excrement until a second ratio of the total amount of the excrement as the representing type of the total amount of excrement.

3. The determination device of claim 1, wherein the computer is configured to:
   determine a type of the excrement being classified according to water content included in the excrement in the target image and confirm the type of a part determined to have the least water content as a representing type for representing the total amount of excrement in a case in which a plurality of parts in the excrement are determined to have different types from each other.

4. The determination device of claim 3,
   wherein the target image is a plurality of images acquired by repeatedly capturing an internal space of a toilet bowl during the excretion in a time series, and
   the computer is configured to:
   extract the target image in which a time-dependent change rate is larger than a second threshold with regard to a relationship between imaging time of each of the plurality of target images and the amount of the excrement, and
   confirm the representing type for representing the total amount based on the type and the amount of the excrement determined in the extracted target image.

5. The determination device of claim 3,
   wherein the target image is a plurality of images acquired by repeatedly capturing an internal space of a toilet bowl during the excretion in a time series, and
   the computer is configured to:
   extract the target image in which a number of times when results determined based on each imaging time of the plurality of target images are consecutively the same with each other is larger than a third threshold, and
   confirm the representing type representing the excrement based on the type of the excrement determined in the extracted target image.

6. The determination device of claim 3,
   wherein the target image is a plurality of images acquired by repeatedly capturing an internal space of a toilet bowl during the excretion in a time series, and
   the computer is configured to:
   confirm the amount of the excrement that is determined to have the most time-dependent amount among the amounts of the excrement determined in each of the plurality of target images and to be the last excrement during the excretion, is the total amount of the excrement during the excretion.

7. The determination device of claim 3, wherein the computer is configured to:
   extract the target image in which a number of times when results determined at each imaging time of the plurality of target images are consecutively the same with each other, is larger than a fourth threshold, and
   confirm a representing type representing the total amount of excrement based on an amount of the excrement determined in the extracted target image.

8. The determination device of claim 3, further comprising an estimator configured to estimate the determination items regarding the excrement in the target image by using an output result of a learned model provided to output a result of determining the determination item regarding the excrement in the input image using a data set associating a learning image in which the excrement is captured and a result of determining the determination item regarding the excrement in the learning image as teacher data, and wherein the computer is configured to determine the determination items using the result estimated by the estimator.

9. The determination device of claim 3, wherein the computer is configured to determine the type of the excrement by a combination of determination results of determining texture, continuity, and edge of the excrement.

10. The determination device of claim 1, wherein the target image is a plurality of images acquired by repeatedly capturing an internal space of a toilet bowl during the excretion in a time series, and the computer is configured to:

extract the target image in which a time-dependent change rate is larger than a second threshold with regard to a relationship between imaging time of each of the plurality of target images and amount of the excrement, and confirm the representing type for representing the total amount based on the type and the amount of the excrement determined in the extracted target image.

11. The determination device of claim 1, wherein the target image is a plurality of images acquired by repeatedly capturing an internal space of a toilet bowl during the excretion in a time series, and the computer is configured to:

extract the target image in which a number of times when results determined based on each imaging time of the plurality of target images are consecutively the same with each other is larger than a third threshold, and confirm the representing type representing the total amount of excrement based on the type of the excrement determined in the extracted target image.

12. The determination device of claim 1, wherein the target image is a plurality of images acquired by repeatedly capturing an internal space of a toilet bowl during the excretion in a time series, and the computer is configured to:

confirm the amount of the excrement that is determined to have the most time-dependent amount among the amounts of the excrement determined in each of the plurality of target images and to be the last excrement during the excretion, is the total amount of the excrement during the excretion.

13. The determination device of claim 1, wherein the computer is configured to:

extract the target image in which a number of times when results determined at each imaging time of the plurality of target images are consecutively the same with each other is larger than a fourth threshold, and confirm a representing type representing the total amount of excrement based on an amount of the excrement determined in the extracted target image.

14. The determination device of claim 1, wherein the computer is further configured to estimate the determination item regarding the excrement in the target image by using an output result of a learned model provided to output a result of determining the determination item regarding the excrement in the input image using a data set associating a learning image in which the excrement is captured and a result of determining the determination item regarding the excrement in the learning image as teacher data, and wherein the computer is configured to determine the determination item using the result estimated by the estimation unit.

15. The determination device of claim 1, wherein the computer is configured to determine the type of the excrement by a combination of determination results of determining texture, continuity, and edge of the excrement.

16. A determination system, comprising:

a toilet device including a toilet bowl;

an imaging device configured to capture an image inside the toilet bowl and output image information including the image; and the determination device of claim 1.

17. A determination method, comprising:

acquiring image information of a target image in which excrement is captured;

determining a type of the excrement in the target image;

selecting a part of the excrement specified according to a time series of excretion; and confirming a representing type for representing a total amount of the excrement by:

determining the total amount of the excrement; and in a case in which a plurality of the parts having different types are included in the excrement, and when an amount of a first part being initially excreted among the plurality of parts having a first type is determined to be larger than a first type threshold corresponding to a first ratio of the initially excreted amount of excrement having the first type to the total amount of the excrement, confirm the type of the initially excreted excrement as the representing type of the total amount of the excrement.

* * * * *